United States Patent [19]

Cavazza et al.

[11] Patent Number: 5,627,212

[45] Date of Patent: May 6, 1997

[54] ESTERS OF L-CARNITINE AND ACYL L-CARNITINE WITH HYDOXY ACIDS FOR PRODUCING PHARMCAEUTICAL COMPOSITIONS FOR TREATING DERMATOSES

[75] Inventors: Claudio Cavazza; Paolo Cavazza, both of Rome, Italy

[73] Assignee: Avantgarde S.p.A., Rome, Italy

[21] Appl. No.: 254,766

[22] Filed: Jun. 6, 1994

[30] Foreign Application Priority Data

Jun. 22, 1993 [IT] Italy .................. RM93A0399

[51] Int. Cl.$^6$ .................. A61K 31/225; A61K 31/22
[52] U.S. Cl. .................. 514/547; 514/551; 510/170
[58] Field of Search .................. 514/547, 551; 560/170

[56] References Cited

U.S. PATENT DOCUMENTS 5,246,967   9/1993   Zezza .................. 514/547
5,418,253   5/1995   Cavazza et al. .................. 514/547

*Primary Examiner*—Porfirio Nazario-Gonzalez
*Assistant Examiner*—Dwayne C. Jones

[57] ABSTRACT

Dermatosis is treated by a method comprising topically applying an effective amount of an ester of L-carnitine or an acyl L-carnitine with a hydroxy carboxylic acid selected from the group consisting of α-hydroxybutyric acid, α-hydroxyisocaproic acid, α-hydroxyisovaleric acid, malic acid and tartronic acid, to a patient in need thereof.

10 Claims, No Drawings

ESTERS OF L-CARNITINE AND ACYL L-CARNITINE WITH HYDOXY ACIDS FOR PRODUCING PHARMCAEUTICAL COMPOSITIONS FOR TREATING DERMATOSES

SUMMARY OF THE INVENTION

The present invention relates to the use of esters of L-carnitine and acyl L-carnitine with hydroxyacids for producing pharmaceutical compositions which contain such esters as active ingredients, suitable to be topically applied For the treatment of dermatoses.

Particularly preferred are the esters of the following hydroxyacids:

α-hydroxybutyric acid
α-hydroxyisobutyric acid
β-hydroxybutyric acid
γ-hydroxybutyric acid
α-hydroxyisocaproic acid
α-hydroxyisovaleric acid
malic acid, and
tartronic acid.

DETAILED DESCRIPTION OF THE PREFERRED EMBODIMENTS

Preferably, the acyl group is $C_{1-5}$ alkanoyl, particularly acetyl, propionyl, butyryl, isobutyryl, valeryl and isovaleryl.

Encompassed by the compounds to be used according to the present invention are both the inner salts and the salts of the aforesaid esters with pharmacologically acceptable acids.

Pharmaceutically acceptable salts of the compound according to the invention include, in addition to the inner salts, all pharmaceutically acceptable salts which are prepared by the addition of acid to L-carnitine, and which do not give rise to undesirable toxic or collateral effects. The formation of pharmaceutically acceptable acid addition salts is well known in pharmaceutical technology.

Non-limiting examples of suitable salts include the chloride, bromide, orotate, acid aspartate, acid citrate, acid phosphate, fumarate, acid fumarate, actate, maleate, acid maleate, acid oxalate, acid sulfate, glucose phosphate, tart rate and acid tartrate salts.

The esters of L-carnitine and the aforesaid alkanoyl L-carnitine with β-hydroxybutyric acid and the pharmacologically acceptable salts thereof are known compounds.

For instance, EP 0443996 A1 discloses the activity of these esters in inhibiting neuronal degeneration (as it occurs e.g. in Alzheimer's dementia and Parkinson's disease) and liver proteolysis and in the treatment of coma.

Also the esters of L-carnitine and the aforesaid alkanoyl L-carnitine with γ-hydroxybutyric acid and the pharmacologically acceptable salts thereof are known compounds (see e.g. EP 429403 A2 and EP 442850 A1). These esters are endowed with the same pharmacological properties as the β-hydroxybutyric acid esters.

On the other hand, the esters of L-carnitine and aforesaid alkanol L-carnitines with hydroxyacids other than β- and γ-hydroxybutyric acid are novel compounds. Their preparation can be carried out similarly to that of the known esters which is disclosed in the aforesaid European patent applications with only slight modifications which, depending on the selected hydroxyacid, will be apparent to any average-skilled expert in organic synthesis.

The preparation of some of the esters suitable for the dermatologic use acceding to the present invention is hereinbelow described.

EXAMPLE 1

Preparation of the ester of L-carnitine with gamma-hydroxybutyric acid (ST 701).

Step a: Preparation of the benzyl ester of gamma-bromobutyric acid.

Gamma-bromobutyric acid (3.3 g; 0.02 moles) was suspended in benzyl alcohol (15 mL). The suspension was cooled to 0° C. and thionyl chloride (8 mL; 0.01 moles) was slowly added dropwise thereto.

The resulting mixture was kept at room temperature for 16 hours, then concentrated under vacuum for removing the thionyl chloride and distilled For removing the benzyl alcohol. The distillation residue was shown to be the title compound.

TLC exane 6—AcOEt4 $R_f$=0.8

NMR $CDCl_3$ δ 7.2(5H,s,aromatic); 5.0(2H,s,$CH_2$-benzyl) 3.3(2H,t,$CH_2$COO); 2.6–2.0(4H,m,Br$CH_2CH_2$)

Step b: Preparation of L-carnitine ester with benzyl gamma-bromobutyrate

Carnitine inner salt (0.8 g; 0.005 moles) was suspended in 10 mL anhydrous dimethyl formamide. Benzyl ester of gamma-bromobutyric acid (1.3 g; 0.005 moles) was added to the suspension. The resulting reaction mixture was kept under stirring at 60° C. for 48 hours under a nitrogen stream and then distilled under vacuum till complete solvent removal; 1.3 g of residue were obtained which was shown to be the title compound.

TLC $CHCL_3$ 4.2-$H_2O$ 1.1-Isopr OH 0.7-$CH_3COOH$ 1.1 MetOH 2.8 $R_f$=0.8

NMR $D_2O$ δ 7.4(5H,s,aromatic); 5.2(2H,s,$CH_2$-benzyl); 4.6(1H,m,$C\underline{H}$OH); 4.2(2H,m,O—$CH_2$); 3.6(2H,m,N+$Ch_2$); 3.3(9H,s,($CH_3)_3$N+); 3.0 (2H,d,CH—$C\underline{H_2}$COO); 2.6(2H,m, $CH_2$ $C\underline{H_2}$COO); 2.0(2H,m,$CH_2$ $C\underline{H_2}CH_2$).

Step c: Preparation of the ester of L-carnitine bromide with gamma-hydroxybutyric acid.

The compound of step b (1.3 g) was dissolved in 20 mL of a 1:1 $H_2O$:EtOH mixture. The resulting solution was hydrogenated in the presence of 150 mg 10% Pd/C at 3 atmospheres of hydrogen for 2 hours. The mixture was filtered and concentrated under vacuum. 1 g of the title compound was obtained.

TLC as in step b $R_f$=0.6

Step d: Preparation of the ester of L-carnitine chloride with gamma-hydroxybutyric acid (ST 701).

The compound of step c (1 g) was eluted on 30 mL of AMBERLITE IRA 402 strongly basic resin activated to Cl⁻ form. The eluate was lyophilized. A highly hygroscopic solid was obtained.

NMR ($D_2O$):δ 4.2(2H,t.—$CH_2$O—); 3.5(2H,d,—N+$Ch_2$—); 3.2(9H,s,($CH_3)_3$ N+); 2.0(2H,d,$CH_2$COO); 2.4(2H, m,$C\underline{H_2}$COOH); 2.0(2H,m,$C\underline{H_2}$—$CH_2COOH$).

$[\alpha]_D = -13.2°$ ( $C = 1, H_2O$)

HPLC
Spherisorb column—SCX 5M
Eluant $KH_2PO_4$ 0.005M—$CH_3CN$ (35–65); pH=4.2
Flow rate 1 ml/min
Detector UV 205 nm
ST 701 $R_T$=7.8
Carnitine $R_T$=10.02 0.5%

Synthesis Scheme of the L-Carnitine Ester
of δ-Hydroxybutyric Acid

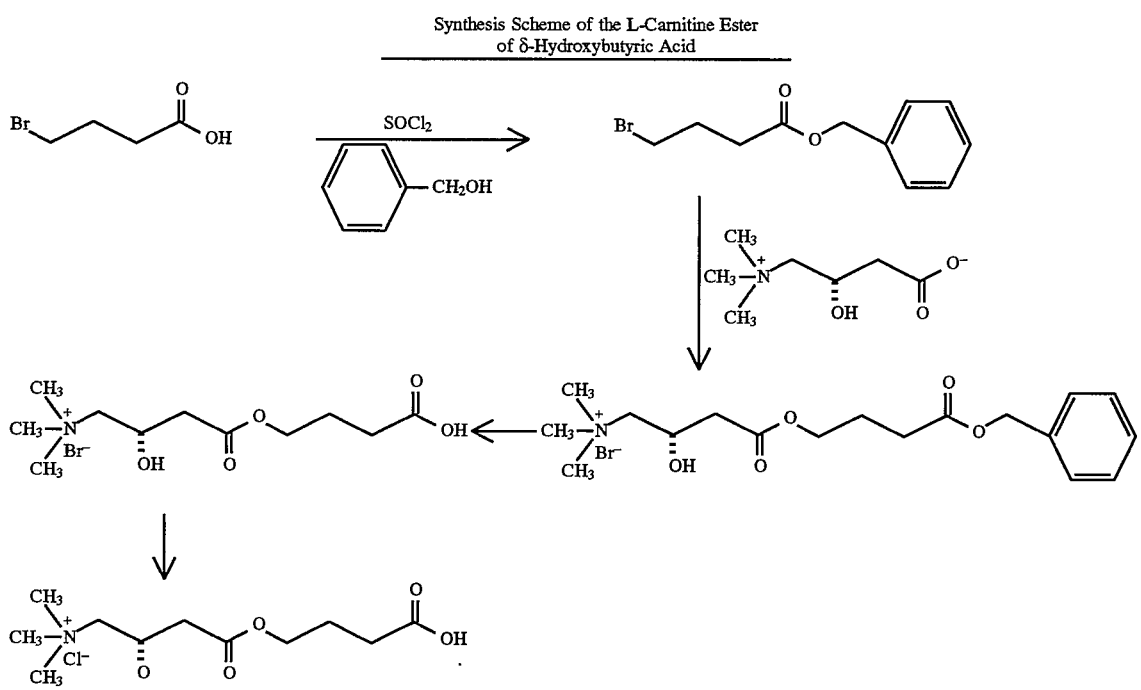

EXAMPLE 2

Preparation of the ester of acetyl L-carnitine with γ-hydroxybutyric acid (ST 793)

Step a: Preparation of the benzyl ester of γ-bromobutyric acid (ST 793).

γ-bromobutyric acid (3.3 g; 0.02 moles) was suspended in benzyl alcohol (15 mL). The suspension was cooled to 0° C. and thionyl chloride (8 mL; 0.01 moles) was slowly added dropwise thereto. The resulting mixture was kept at room temperature for 16 hours, then concentrated under vacuum to remove the unreacted thionyl chloride and distilled to remove the benzyl alcohol. The distillation residue was purified by silica gel chromatography using hexane-AcOEt 98:2 as eluant.

TLC hexane $R_f$=0–2

NMR CDCl$_3$ δ 7.2(5H,s,aromatic); 5.0(2H,s,CH$_2$-benzyl) 3.3(2H,t,CH$_2$COO); 2.6–2.0(4H,m,BrCH$_2$CH$_2$)

Step b: Preparation of the ester of acetyl L-carnitine with benzyl γ-bromobutyrate.

Acetyl L-carnitine inner salt (1.62 g; 0.008 moles) was suspended in 12 mL anhydrous dimethylformamide. γ-bromobutyric acid benzyl ester (2.05 g; 0.008 moles) was added to the suspension.

The resulting reaction mixture was kept under stirring for 24 hours under a nitrogen stream.

Ethyl ether was then added till complete precipitation of a compound which was filtered off. 3.43 g of the title compound were thus obtained.

TLC CHCl$_3$ 4.2-H$_2$O 1.1-Isopr OH 0,7-Ch$_3$COOH 1.1 MetOH 2.8 $R_f$=0.8

HPLC
Column μ Bondapack C18
eluant KH$_2$PO$_4$ 0.05M—CH$_3$CN 70-30
Flow rate 1 mL/min
$R_t$ 12.9

NMR D$_2$O δ 7.4 (5H,s,aromatic); 5.6(1H,m,

CH)
|
OCO 5.2(2H,s,CH$_2$-benzyl); 4.4–4.0(4H,m,N+CH$_2$,OCH$_2$) 3.5 (9H,s,(CH$_3$)$_3$N+); 3.2(2H,d,CH—CH$_2$COO); 2.3(2H,m, CH$_2$CH$_2$COO); 2.0(5H,m+,CH$_2$CH$_2$CH$_2$;COCH$_3$)

Step c: Preparation of the ester of acetyl L-carnitine bromide with γ-hydroxybutyric acid.

The compound of the step b (1 g) was dissolved in 20 mL absolute ethanol. The resulting solution was hydrogenated in the presence of 100 mg 10% Pd7C at 3 atmospheres of hydrogen concentrated under vacuum. 0.75 g of the title compound were obtained. Yeld 98%.

TLC as in step b $R_f$=0.7

Step d: Preparation of the ester of acetyl L-carnitine with γ-hydroxybutyruic acid inner salt.

The compound of step c (1 g) was eluted on 30 mL of a strongly basic resin AMBERLITE IRA 402 activated in HCO$_3^-$ form. The eluate was lyophilized. A highly hygroscopic solid was obtained.

NMR (D$_2$O): δ 5.6(1H,m,

CH);
|
OCO 4.2(2H,t,—CH$_2$O); 3.7(2H,d,—N+CH$_2$—); 3.2(9H,s,(CH$_3$) $_3$N+); 2.8(2H,d,CH$_2$COO); 2.3–2.0(5H,m+s,CH$_2$COOH+ COCH$_3$); 1.8(2H,m,CH$_2$CH$_2$COOH)

[α]$_D$= –18.0 (C = 1, H$_2$O)

HPLC
Column spherisorb—SCX 5M
Eluant KH$_2$PO$_4$0.005M—CH$_3$CN (35–65); pH=4.2

Flow-rate 1 mL/min
Detector UV 205 nm
Rt=8.83
TLC as in step b $R_F$=0.5

EXAMPLE 3

Preparation of the ester of isovaleryl L-carnitine chloride with β-hydroxybutyric acid (ST 687)

Step a: Preparation of the benzyl ester of β-hydroxybutyric acid 1.

β-hydroxybutyric acid sodium salt (1.2 g; 0.01 moles) was suspended in benzyl bromide (6 mL; 0.05 moles) 18 crown-6 (0.264 g) dissolved in 7 mL acetonitrile was added to the mixture.

The resulting solution was partly concentrated under a nitrogen stream and then kept under stirring at 80° C. for 90 minutes. To the cooled solution a mixture hexane-$H_2O$ was added. The separated and dried organic phase was concentrated and then distilled under vacuum for removing the excess benzyl bromide.

1.1 g of solid residue were obtained which was identified to be the title compound. Yield 56%.

TLC $CHCl_3$ 9—MetOH 1 $R_F$=0.8

Gas chromatography: column $HP_1$ 25 m; inner diameter 0.32 mm; film thickness 0.33 μm carrier (He) flow-rate: 1 mL/min.
Make up gas 40 mL/min
Splitting ration 40 mL/min
Injector 220° C.
Detector (Fid) 280° C.
Column temperature 120° C., 15° C./min 250° C.
Rt=9.36 compound
Rt=4.84 no benzyl bromide NMR $CDC_3$ δ 7.3(5H,s,benzyl); 5.2(2H,s,$CH_2$-benzyl); 4.2(1H,m,CH); 2.8(1H,s,broadOH); 2.5(2H,d,$CH_2$COO); 1.2(3H,d,$CH_3$)

Step b: Preparation of the acid chloride of isovaleryl L-carnitine chloride 2.

Thionyl chloride (7.7 mL; 0.1 moles) was added to isovaleryl L-carnitine chloride (10 g; 0.035 moles). The resulting mixture was kept at room temperature for 4 hours, then concentrated under vacuum to remove the thionyl chloride excess. The residue was washed three times with anhydrous ethyl ether.

The raw reaction product thus obtained was used in the subsequent step without further purification.

Step c: Preparation of the ester of isovaleryl L-carnitine choride with β-hydroxybutyric acid benzyl ester 3.

The acid chloride of isovaleryl L-carnitine chloride (0.035 moles) of step b was dissolved in anhydrous tetrahydrofuran (25 mL). To the resulting solution the β-hydroxybutyric acid benzyl ester (7 g; 0.035 moles) of step a was added.

The reaction mixture was kept at 25° C. under stirring overnight.

Ethyl ether was then added thereto till complete precipitation. The solid thus obtained was filtered off and washed with ethyl ester. 14 g of the title compound were obtained. Yield 89%.

NMR $D_2O$ δ5.7(5H,m,benzyl); 5,5(1H,m,—CH—); 5.2 (1H,m,COOCH); 5.0(2H,s,$CH_2$benz.) 3.8(2H,m,$NCH_2$); 3.2 (9H,s,($H_3)_3$N+); 2.8–2.5(4H,dd,$CH_2$—COOCHCH$_2$COO); 2.2(2H,d,$OCOCH_2$) 1.8(1H,m,

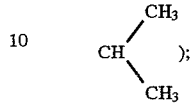

1.2(3H,d,CH—$CH_3$); 0.8(6H,d,

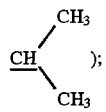

Step d: Preparation of the ester of isovaleryl L-carnitine chloride with β-hydroxybutyric acid The compound of step c (14 g; 0.031 moles) was dissolved in $H_2O$-ethanol 1:1 (100 mL) and hydrogenated in the presence of 1,5 g 10% Pd/C at 4 atmospheres for two hours.

The reaction mixture was filtered, the filtrate concentrated to dryness under vacuum and the residue crystallized from acetone-ethyl ether. 10 g of a hygroscopic compound were obtained.

TLC chloroform 4.2 IsoprOH 0.7 MeOH 2.8 $H_2O$1 AcOH 1.1 Rf=0.7

$[α]_D$ = −21°  (C = 1, $H_2O$)

$NMRD_2O$ δ 5.7(1H,m,

CH);
|
OCO 5.3(1H,m,—COOCH—); 3.8(2H,m,N+$CH_2$) 3.2(9H,s, $(CH_3)_3$N+); 2.8(2H,d,$CH_2$—COO); 2.6(2H,d,$CH_2$COOH); 2.2(2H,d,$OCOCH_2$);1.8(1H,m,

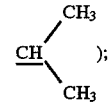

1.2(3H,d,CH$CH_3$); 0.8(6H,d,

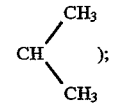

HPLC
Column μ Bondapack-C18
Eluant $KH_2 PO_4$ 0.05M—$CH_3CN$ (85–15)
Detector UV λ=205 nm
Flow-rate 1 ml/min
Rt=14–16 (the diasteroisomers are shown)

| Elementary Analysis for $C_{15}H_{30}NO_6Cl$ | | | |
|---|---|---|---|
| | C | H | N |
| calc. | 50.6 | 8.4 | 3.9 |
| found | 48.93 | 8.36 | 3.49 |

The dermatoses which are suitably treated with the compositions of the present invention are in particular ichthyosis, psoriasis and those dermatoses which are induced by a defective keratinization, such as dandruff, acne and palmar and plantar hyperkeratosis.

Ichthysosis is a dermatosis characterized by generalized dryness, harshness and scaling of the skin. It may occur as a hereditary disease present at birth, or as a metabolic disorder associated with hypothyroidism or with the intake of drugs (such as butyrophenols) inhibiting lipid synthesis, or as a paraneoplastic syndrome, manifestation of a tumor process involving internal organs.

Xeroderma, the mildest form of ichthyosis is neither congenital nor associated with systemic abnormalities.

It usually occurs on the lower lees of middle-aged or older patients, most often in cold weather and in patients who bathe frequently. There may be mild to moderate itching and an associated dermatitis due to detergents or other irritants.

The inherited ichthyoses, all characterized by excessive accumulation of scale on the skin surface, are classified according to clinical, genetic, and histologic criteria.

Known treatments of and form of ichthyosis comprise topically applying to the skin hydrating emollients. Furthermore, salicylic acid or vitamin A-containing ointments have been widely used.

A keratolytic agent particularly effective in removing the scale in ichthyosis vulgaris, lamellar ichthyosis and sex-linked ichthyosis contains 6% salicylic acid in a gel composed of propylene glycol, ethyl alcohol, hydroxypropylene cellulose and water.

Further known drugs for the treatment of this disorder include: 50% propylene glycol in water, hydrophilic petrolatum and water (in equal parts), and cold cream and an a-hydroxy acid (e.g. lactic and pyruvic acid) in various bases. In lamellar ichthyosis, 0.1% tretinoin (vitamin A acid; retinoic acid) cream has been utilized. None of these treatments has been found satisfactorily effective.

Hyperkeratosis is a thickening of the stratum corneum of the skin.

The treatment of choice is the topical application of drugs containing urea, propylene glycol or salicylic acid. Also in this case, none of the known treatment has proved to be satisfactorily effective.

It has now been found that the compounds of the present invention, when topically applied as solutions, lotions, creams or ointments containing from 0.01% to 20%, preferably from 1% to 15% and most preferably from 2 to 10% by weight of at least one of the foregoing compounds, are potently effective in achieving complete remission of ichthyotic conditions in humans and in healing psoriasis and those disorders brought about by an altered keratinization, such as dandruff, acne and palmar and plantar hyperkeratosis.

It has also been found that, if the solutions, creams or ointments of the invention are applied regularly on a daily basis, within about two to three weeks the effected skin areas will return to normal conditions.

The compounds according to the invention are prepared via a process whose steps are illustrated in the following reaction scheme, wherein R, $R_1$ and X have the previously defined meanings.

In order to prepare the compositions of this invention, at least one of the esters according to the invention is preferably dissolved in water or ethanol initially. The solution thus prepared may be admixed in the conventional manner with commonly available ointment bases such as hydrophilic ointment (USP) or petrolatum (USP).

The water or ethanol used to dissolve the compounds according to this invention may range in concentration of from 1 to 30%, by volume, of the total composition.

The compounds of this invention may also be formulated in a solution or lotion form.

For instance, an ester according to the invention is dissolved directly in a mixture of water, ethanol and propylene glicol (40:40:20 by weight).

Some examples of the formulation are hereinbelow described:

Formulation 1:5% Solution 5 grams of an ester according to the invention were dissolved in 5 mL of water and the resulting solution admixed with 40 mL of ethanol and 20 mL of propylene glycol. Sufficient water was added to make 100 mL of formulation.

Formulation 2:5% Ointment 5 grams of an ester according to the invention were admixed with 95 grams of USP grade hydrophilic ointment, until an uniform consistency resulted.

We claim:

1. A method of treating dermatosis comprising: topically applying an effective amount of an ester of L-carnitine or an acyl L-carnitine with a hydroxy carboxylic acid selected from the group consisting of α-hydroxybutyric acid, α-hydroxyisocaproic acid, α-hydroxyisovaleric acid, malic acid and tartronic acid, said acyl group being a $C_{1-5}$ alkanoyl radical selected from the group consisting of acetyl, propionyl, butyryl, isobutyryl, valeryl and isovaleryl, and the pharmaceutically acceptable salts of said esters, to a patient in need thereof.

2. The method of claim 1, wherein the esters of L-carnitine and said acyl L-carnitine are in the form of inner salts.

3. The method of claim 1, wherein said dermatosis arises from ichthyosis or psoriasis.

4. The method of claim 1, wherein said dermatosis condition is brought about by defective keratinization.

5. The method of claim 1, wherein said dermatosis condition is dandruff, acne, or palmar or plantar hyperkeratosis.

6. A pharmaceutical composition for topical administration in the treatment of dermatosis, which comprises:

an ester of L-carnitine or acyl L-carnitine with a hydroxy carboxylic acid selected from the group consisting of α-hydroxyisocaproic acid, α-hydroxyisovaleric acid, malic acid and tartronic acid, said acyl group being a $C_{1-5}$ alkanoyl selected from the group consisting of acetyl, propionyl, butyryl, isobutyryl, valeryl and isovaleryl, and the pharmaceutically acceptable salts thereof in combination with a pharmaceutically acceptable excipient.

7. The composition of claim 6, wherein the composition is in the form of a solution, lotion, ointment or cream.

8. The composition of claim 6, wherein the content of active ester compound ranges from 0.01% to 20% by weight.

9. The composition of claim 8, wherein the amount of said active ester ranges from 1% to 15% by weight.

10. The composition of claim 9, wherein the amount of said active ester ranges from 2% to 10% by weight.

* * * * *